(12) United States Patent
Thies et al.

(10) Patent No.: US 9,789,189 B2
(45) Date of Patent: Oct. 17, 2017

(54) DRUG DELIVERY COMPOSITION COMPRISING PROTEINS AND BIODEGRADABLE POLYESTERAMIDES

(71) Applicant: DSM IP ASSETS B.V., Heerlen (NL)

(72) Inventors: Jens Christoph Thies, Echt (NL); George Mihov, Echt (NL); Guy Draaisma, Echt (NL)

(73) Assignee: DSM IP ASSETS BV, Heerlen (NL)

( * ) Notice: Subject to any disclaimer, the term of this patent is extended or adjusted under 35 U.S.C. 154(b) by 0 days.

(21) Appl. No.: 14/425,487

(22) PCT Filed: Oct. 2, 2013

(86) PCT No.: PCT/EP2013/070543
§ 371 (c)(1),
(2) Date: Mar. 3, 2015

(87) PCT Pub. No.: WO2014/053542
PCT Pub. Date: Apr. 10, 2014

(65) Prior Publication Data
US 2015/0216987 A1    Aug. 6, 2015

(30) Foreign Application Priority Data

Oct. 2, 2012  (EP) .................................. 12186915
Jun. 25, 2013 (EP) .................................. 13173634

(51) Int. Cl.
  A61K 47/34   (2006.01)
  A61K 47/30   (2006.01)
  A61K 47/42   (2006.01)
  C08G 69/44   (2006.01)
  C08L 77/12   (2006.01)
  A61K 38/44   (2006.01)

(52) U.S. Cl.
  CPC .............. *A61K 47/34* (2013.01); *A61K 38/44* (2013.01); *C08G 69/44* (2013.01); *C08L 77/12* (2013.01); *C12Y 111/01007* (2013.01)

(58) Field of Classification Search
  CPC ......... A61K 47/34; A61K 47/30; A61K 47/42
  See application file for complete search history.

(56) References Cited

U.S. PATENT DOCUMENTS

| 4,550,730 A | 11/1985 | Shalaby et al. |
| 6,503,538 B1 | 1/2003 | Chu et al. |
| 2004/0063606 A1 | 4/2004 | Chu et al. |
| 2004/0170685 A1 | 9/2004 | Carpenter et al. |
| 2005/0271700 A1 | 12/2005 | DesNoyer et al. |
| 2006/0009498 A1 | 1/2006 | Whitcup |
| 2006/0024357 A1 | 2/2006 | Carpenter et al. |
| 2006/0093842 A1 | 5/2006 | DesNoyer et al. |
| 2006/0159918 A1 | 7/2006 | Dugan et al. |
| 2006/0177416 A1 | 8/2006 | Turnell et al. |
| 2007/0077272 A1 | 4/2007 | Li et al. |
| 2007/0134332 A1 | 6/2007 | Turnell et al. |
| 2007/0282011 A1 | 12/2007 | Gomurashvili et al. |
| 2007/0292476 A1 | 12/2007 | Landis et al. |
| 2008/0057024 A1 | 3/2008 | Zhang et al. |
| 2008/0299174 A1 | 12/2008 | Gomurashvili et al. |
| 2009/0232874 A1 | 9/2009 | Chu et al. |
| 2009/0253809 A1 | 10/2009 | Gomurashvili et al. |
| 2012/0282299 A1 | 11/2012 | Delamarre et al. |
| 2014/0105957 A1 | 4/2014 | Franken et al. |
| 2014/0120170 A1 | 5/2014 | Mihov et al. |
| 2014/0179802 A1 | 6/2014 | Franken et al. |
| 2014/0220099 A1* | 8/2014 | Draaisma ............... C08G 69/44 424/443 |
| 2015/0038415 A1 | 2/2015 | Zupancich |
| 2015/0216987 A1 | 8/2015 | Thies et al. |
| 2015/0240387 A1 | 8/2015 | Gillissen-Van Der Vight et al. |

(Continued)

FOREIGN PATENT DOCUMENTS

| CA | 2 419 429 | 3/2003 |
| CN | 1837259 | 9/2006 |
| CN | 101168595 | 10/2006 |

(Continued)

OTHER PUBLICATIONS

International Search Report for PCT/EP2013/070543, mailed Oct. 29, 2013.
Tsitlanadze, G. et al., "Biodegradation of amino-acid-based poly-(ester amide)s: in vitro weight loss and preliminary in vivo studies", Journal of Biomaterials Science, vol. 15, (Jan. 1, 2004), 24 pages.
Eccleston et al., pH-responsive pseudo-peptides for cell membrane disruption, Journal of Controlled Release, 2000, pp. 297-307, vol. 69, No. 2.
Eccleston et al., Synthetic routes to responsive polymers, Reactive & Functional Polymers, 1999, pp. 147-161, vol. 42, No. 2.
Gautier et al., Alkylated poly(L-lysine citramide) as models to investigate the ability, Journal of Controlled release, 1999, pp. 235-247, vol. 60, No. 2-3.

(Continued)

Primary Examiner — Michael B Pallay
(74) Attorney, Agent, or Firm — Kevin M. Bull

(57) ABSTRACT

Drug delivery compositions are provided having proteins and biodegradable polymers that may be used for controlled and long term release of proteins into a biological environment. According to some embodiments, the drug delivery composition may be provided with at least a protein and a biodegradable polymer possessing at least two different functional groups selected from the group of chosen among carboxyl, ester, amine, amide, thiol, thioester or hydroxyl groups pendant to the main polymer chain whereby the composition absorbs between 5-10% w/w water when exposed to physiological conditions for at least 20 days. A drug delivery system for controlled protein release which includes the drug delivery composition is also provided whereby the drug delivery system may be in the form of microparticles, films, coatings, fibers, pellets, cylinders, discs, implants, microcapsules, microspheres, nanospheres, wafers, micelles, liposomes or woven or non-woven fabrics.

20 Claims, 6 Drawing Sheets

(56) References Cited

U.S. PATENT DOCUMENTS

Figure 1:
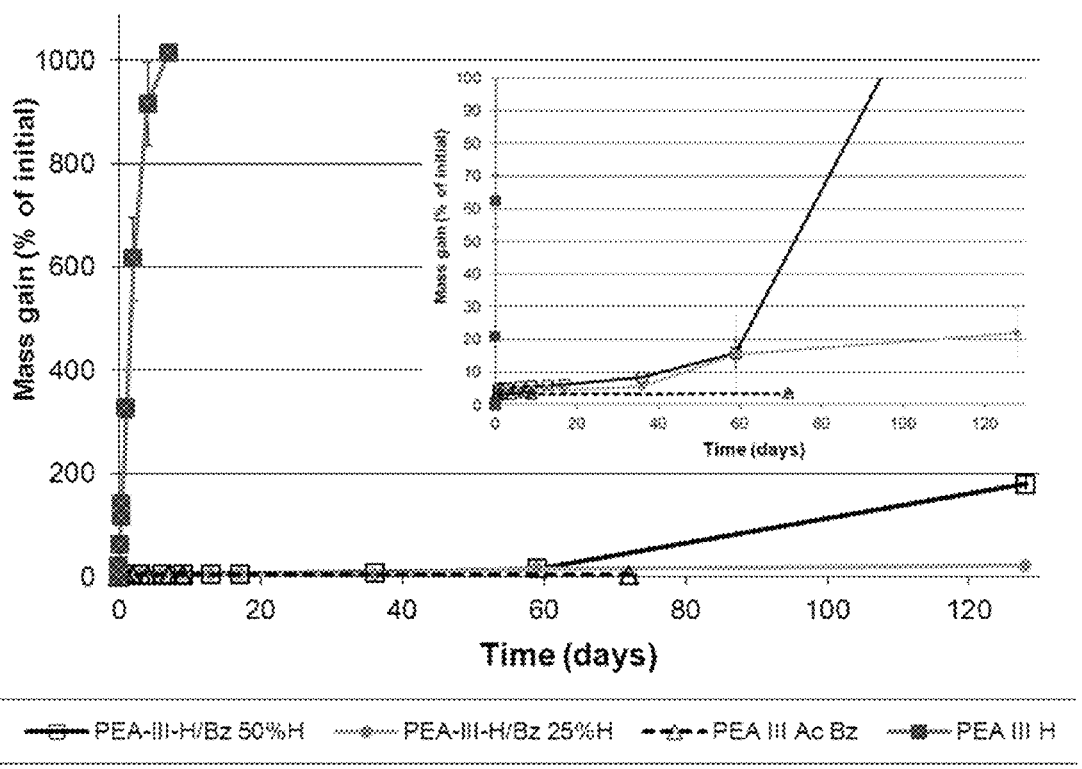

| | | | |
|---|---|---|---|
| 2015/0246001 A1 | 9/2015 | Zupancich et al. | |
| 2015/0328374 A1 | 11/2015 | Mihov et al. | |

FOREIGN PATENT DOCUMENTS

| | | | |
|---|---|---|---|
| CN | 103619910 | 3/2014 | |
| CN | 103748139 | 4/2014 | |
| EP | 0926184 | 12/1998 | |
| EP | 0926184 | 6/1999 | |
| JP | 2005139139 | 6/2005 | |
| NL | WO 2011045443 A1 * | 4/2011 | ............ A61L 27/34 |
| WO | WO 02/18477 | 3/2002 | |
| WO | WO2002018477 A2 | 3/2002 | |
| WO | 20070089931 | 8/2007 | |
| WO | WO2007089931 | 8/2007 | |
| WO | WO2007130477 | 11/2007 | |
| WO | 20080048298 | 4/2008 | |
| WO | WO2008048298 | 4/2008 | |
| WO | 2008/157254 | 12/2008 | |
| WO | WO2009012449 A1 | 1/2009 | |
| WO | WO2011045443 A1 | 4/2011 | |
| WO | WO2011146483 | 11/2011 | |
| WO | 2012/175746 | 12/2012 | |
| WO | 2012/175748 | 12/2012 | |
| WO | WO2012175748 | 12/2012 | |

OTHER PUBLICATIONS

May 19, 2016 Non-Final Ofice Action in U.S. Appl. No. 14/653,137.
Nov. 9, 2016 Non-Final Office Action in U.S. Appl. No. 14/432,349.
Aug. 9, 2016 Non-Final Office Action in U.S. Appl. No. 14/128,839.
USPTO, Non Final Office Action, dated Jan. 30, 2017.
USPTO, Non Final Office Action, dated Feb. 13, 2017.
Non Final office Action U.S. Appl. No. 15/252,350 dated Aug. 17, 2017.
Non Final office Action U.S. Appl. No. 14/432,349 dated Aug. 23, 2017.

* cited by examiner

DRUG DELIVERY COMPOSITION COMPRISING PROTEINS AND BIODEGRADABLE POLYESTERAMIDES

This application is the U.S. national phase of International Application No. PCT/EP2013/070543, filed 2 Oct. 2013, which designated the U.S. and claims priority to EP Application No. 12186915.0, filed on 2 Oct. 2012, and EP Application No. 13173634.0, filed on 25 Jun. 2013, the entire contents of each of which are hereby incorporated by reference.

The present invention relates to a drug delivery composition comprising proteins and biodegradable polyesteramides. The present invention further relates to a drug delivery system for controlled and long term release of proteins into a biological environment.

In the prior art proteins are typically administered by repeated injection or by infusion because of their poor oral bioavailability and short in vivo half-lives and thus posing a significant physical burden on the patient and associated administrative costs. As such, there was a great deal of interest in developing and evaluating controlled-release formulations. For example in Zhao and Topp, Recent Patents on Drug delivery & formulation, 2008, vol. 2, (3), an overview is given on developments in controlled release of protein formulations. Controlled release formulations offer protection from in vivo degradation and elimination, decreased toxicity, improve patient compliance, the ability to localize or target the protein to a particular site, and more efficient use of the protein resulting in lower dosages. Despite the extensive research, the progress in controlled release of proteins is hampered by number of technical challenges such as protein denaturing during formulation process, loss of activity in the course of prolonged in vivo release, burst release, incomplete release, protein aggregation and related immunogenicity, low encapsulation efficiency and formulation complexity. Burst release occurs when the delivery system releases more of the proteins than is desirable at a given time. Incomplete release occurs when most of the protein initially incorporated in a polymer matrix is not released while protein elution from the delivery system is already terminated.

The use of polymers for the release of proteins have been widely tested and most of the polymer based protein releasing solid forms do limit the initial burst release and the unnecessary patient exposure to high protein concentrations but suffer from incomplete release due to poor diffusion of the proteins out of the polymer matrix. The problem of an incomplete release of proteins has been solved by the use of hydrogel based drug delivery systems such as for example disclosed in WO0000222. However hydrogels do not provide a controlled protein release for a period longer than a few weeks.

Also biodegradable polymers such as alpha-hydroxy acid based polyesters for example polylactides (PLLA) or poly-lactic-glycolic acid copolymers (PLGA) are widely explored as polymer matrixes for sustained release of proteins. PLLA or PLGA however face problems with protein stability due to acidic byproducts released during the polymer degradation. This has been confirmed in FIG. 4.

The stability of proteins is furthermore influenced by harsh fabrication conditions when preparing protein delivery formulations, for example, exposure to organic solvents, air-liquid interface, vigorous agitation, sonication, etc.

The object of the present invention is therefore to provide a drug delivery compositions and drug delivery systems made thereof which are both safe and deliver proteins in a more controlled manner. Additionally, it is the object of the present invention to prolong the protein delivery from the drug delivery system over several months.

The object of the present invention is achieved by providing a drug delivery composition comprising at least a protein and a biodegradable polymer possessing at least two different functional groups selected from the group of carboxyl-, ester-, amine-, amide-, thiol-, thioester- or hydroxyl groups, pendant to the polymer backbone whereby the polymer absorbs between 2-20% w/w water when exposed to physiological conditions for 20 days.

Surprisingly it has been found that the different functional groups and their relative ratio in the polymer backbone maintain the interaction of the polymer matrix with water molecules and control the sustained release of the protein. It is important in the present invention that the absorption of water molecules into the polymer matrix occurs slowly, because this will result in slowly opening the polymer matrix and providing a sustained release of the proteins over a period of months to years at physiological conditions.

Preferably the polymer absorbs between 4-15% w/w water when exposed to physiological conditions for 20 days. More preferably the polymer absorbs between 4-10% w/w water when exposed to physiological conditions for 20 days.

The absorption of water is critical for the complete liberation of protein molecules from the polymer matrix. For example in swollen hydrogels the mass fraction of water is much higher than the fraction of polymer. This means that the water absorption significantly exceeds 100% (w/w), typically in the range of 1000-10000% (w/w). Furthermore, the water absorption and respectively the swelling of hydrogels occur for a period from several hours up to a week upon exposure of the polymer to aqueous environment. Unlike as typical hydrogels, which typically absorb more than 100% (w/w) water, the composition according to the present invention absorbs only between 4-10% w/w water when exposed to physiological conditions for 20 days. Physiological conditions mean in an aqueous medium at 37° C., pH 7.2-7.4, and ion strength equivalent to 0.9% NaCl solution in water.

Preferably the two different functional groups comprise at least an unprotected hydrophilic functional group chosen from a carboxyl-, amine or hydroxyl group and at least a protected hydrophobic functional group chosen from an ester, amide-, thiol- or thioester group. Unprotected means a free carboxylic group or —COOH group, —NH2 group or —OH group. By the protected hydrophobic functional group is meant a —COOR group, a —COSR, a —CONHR, a —COC(O)R, a —CSC(O)R, a NHC(O)R or a —SR group in which R can be a ($C_1$-$C_{20}$) alkyl group or a ($C_6$-$C_{10}$) aryl ($C_1$-$C_6$)alkyl group.

The ratio of unprotected hydrophilic groups to protected hydrophobic functional groups preferably varies from 0.17-3, more preferably 0.3-1.

More preferably the composition according to the present invention comprises a biodegradable polymer which possesses pendant unprotected carboxyl- and protected ester functional groups.

In a preferred embodiment the biodegradable polymer is a biodegradable polyesteramide copolymer (PEA) according to structural Formula (I),

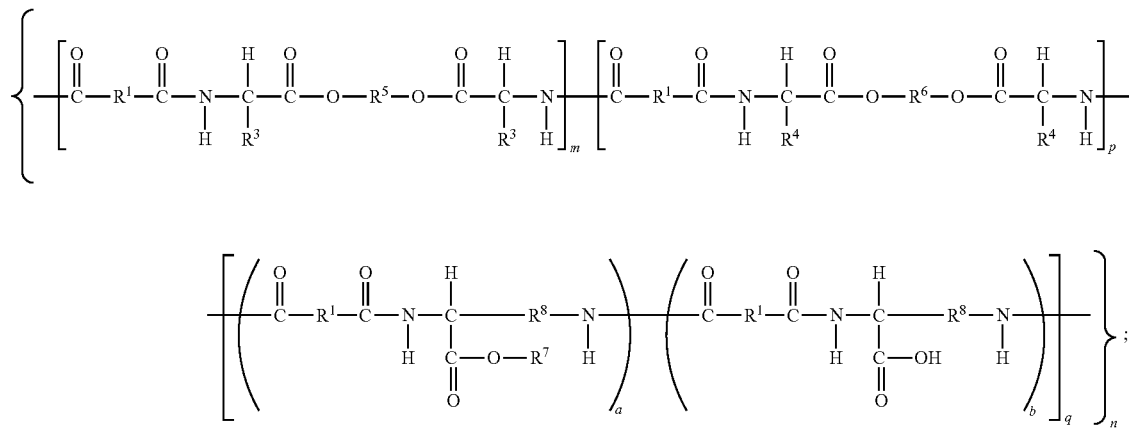

Formula I wherein m+p varies from 0.9-0.1 and q varies from 0.1 to 0.9; m+p+q=1 whereby m or p could be 0; n varies from 5 to 300 and wherein a is at least 0.1, b is at least 0.15 and a+b=1
and whereby:

$R_1$ is independently selected from the group consisting of $(C_2-C_{20})$ alkyl or $(C_2-C_{20})$ alkylene.

$R_3$ and $R_4$ in a single backbone unit m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $-(CH_2)SH$, $-(CH_2)_2S(CH_3)$, $-(CH_3)_2-CH-CH_2-$, $-CH(CH_3)_2$, $-CH(CH_3)-CH_2-CH_3)$, $-CH_2-C_6H_5$, $-(CH_2)_4-NH_2$, and mixtures thereof.

$R_5$ is independently selected from the group consisting of $(C_2-C_{20})$alkyl, $(C_2-C_{20})$alkylene.

$R_6$ is selected from bicyclic-fragments of 1,4:3,6-dianhydrohexitols of structural formula (II);

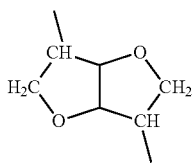

Formula II $R_7$ is independently selected from the group consisting of $(C_6-C_{10})$ aryl $(C_1-C_6)$alkyl or a protecting group.

$R_8$ is $-(CH_2)_4-$.

It has been found that the composition comprising the polyesteramide according to formula (I) in which a protected functional group is present in backbone unit (a) and in which an unprotected functional group is present in the backbone unit (b), whereby the percentage of unprotected functional groups in backbone unit (b) is at least 15% and the total of unprotected and protected functional groups is 100%, provides a uniform and sustained release of proteins over at least 6 weeks. It is moreover observed that the composition lowers the fluctuations in protein release per week. A PEA comprising at least 15% L-lysine-COOH and thus 85% L-Lysine-COO-Benzyl (Bz) is further referred to as PEA-H/Bz 15% H.

The present invention thus relates to a drug delivery composition comprising a protein and biodegradable polyesteramide of Formula (I) which unlike classical hydrogels does not absorb water significantly when exposed to physiological conditions for 20 days which prevents a quick release of the protein load. It was surprisingly observed that the polyesteramide matrix is slowly and continuously absorbing water molecules by water diffusion and hydrolysis driven biodegradation process. This results in a slow opening of the polymer matrix and allows the proteins to diffuse slowly out of the polymer which affords a controlled release of the proteins over a long time. Furthermore it is unexpected that the polyesteramide matrix as well as its byproducts resulting from degradation are highly compatible with the protein species and do not impact their biological activity or stability.

In below illustration from left to right, the release of a dry polymer matrix containing protein is shown. Initial water uptake results in marginal swelling of the matrix resulting in an initial release of the protein. Over time polymer hydrolysis results in a less dense network that gradually takes up more water. A sustained release of protein is achieved eventually a small amount of the protein remains in the matrix until the polymer is completely degraded.

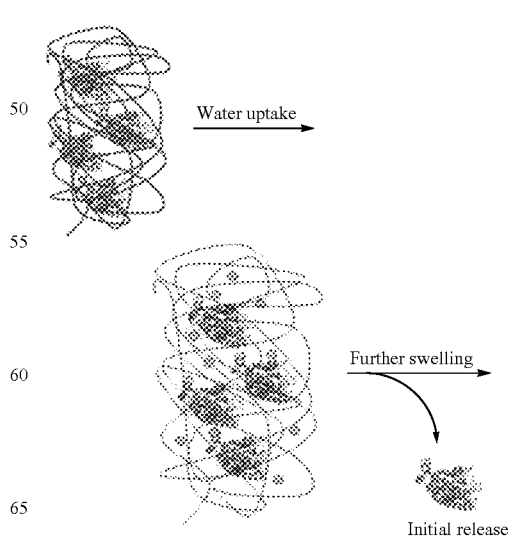

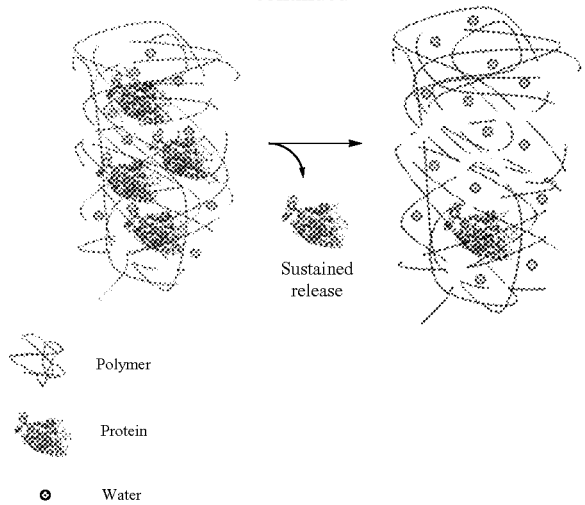

Biodegradable polyesteramides are known in the art and for example disclosed in WO2008/0299174. These PEA's as shown in below Formula III comprise at least two linear saturated or unsaturated aliphatic diol residues into two bis-(a amino acid)-based diol-diesters. The lysine units present in backbone unit q are either protected, in case $R_7$ is benzyl, or unprotected, in case that R7 is H. A PEA comprising unprotected lysine is further indicated as PEA-III-H, a PEA comprising protected lysine further indicated as PEA-III-Bz.

benzyl, $R_8$ is $—(CH_2)_4—$, this polyesteramide is further referred to as PEA-I-H/Bz 50% H.

In another preferred embodiment the biodegradable polyesteramide copolymer according to Formula (I) comprises m+p+q=1, q=0.25, p=0.45 and m=0.3, b is 0.25 and a+b=1 whereby $R_1$—$(CH_2)_8$, $R_3$ and $R_4$ respectively, are $(CH_3)_2$—CH—$CH_2$—, $R_5$ is selected from the group consisting of $(C_2-C_{20})$alkylene, $R_7$ is benzyl, $R_8$ is —$(CH_2)_4$—; $R_6$ is selected from bicyclic-fragments of 1,4:3,6-dianhydrohexitols of structural formula (II), this polyesteramide is referred to as PEA-III-H/Bz 25% H.

In yet another preferred embodiment of the present invention the biodegradable polyesteramide copolymer according to Formula (I) comprises m+p+q=1, q=0.25, p=0.45 and m=0.3, b is 0.5, a+b=1 whereby $R_1$ is —$(CH_2)_8$; $R_4$ is $(CH_3)_2$—CH—$CH_2$—, $R_7$ is benzyl, $R_8$ is —$(CH_2)_4$; $R_6$ is selected from bicyclic-fragments of 1,4:3,6-dianhydrohexitols of structural formula (II), this polyesteramide is further referred to as PEA-III-H/Bz 50% H.

In still another embodiment the biodegradable polyesteramide copolymer according to Formula (I) comprises m+p+q=1, q=0.1, p=0.30 and m=0.6, b is 0.5 and a+b=1 whereby $R_1$—$(CH_2)_4$, $R_3$ and $R_4$ respectively, are $(CH_3)_2$—CH—$CH_2$—; $R_7$ benzyl, $R_8$ is —$(CH_2)_4$—, $R_5$ is selected from the group consisting of $(C_2-C_{20})$alkylene, $R_6$ is selected from bicyclic-fragments of 1,4:3,6-dianhydrohexitols of structural formula (II); this polyesteramide is further referred to as PEA-II-H/Bz 50% H.

At least one of the alpha-amino acids used in the polyesteramide co-polymers is a natural alpha-amino acid. For example, when the $R_3$s or $R_4$s are $CH_2Ph$, the natural Formula III

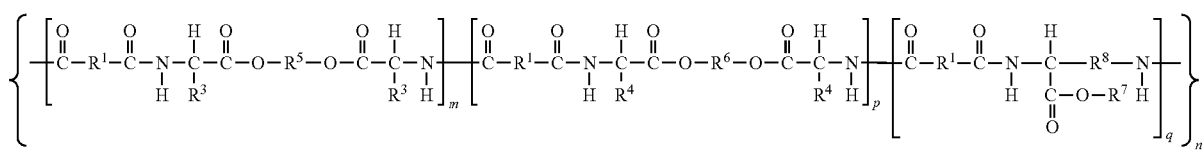

In Formula III m varies from 0.01 to 0.99; p varies from 0.2 to 3 and q varies from 0.10 to 1.00 whereby n is 5 to 100; $R_1$ is —(CH2)8; $R_3$ and $R_4$ in the backbone units m and p is leucine, —$R_5$ is hexane, and $R_6$ is a bicyclic-fragments of 1,4:3,6-dianhydrohexitols of structural formula (II); $R_7$ may be chosen from H or a benzyl group and $R_8$ is —(CH2)4-.

It has been recognized that PEA-III-H shows high swelling profiles which result in a quick burst release of any loaded or encapsulated bioactive agents in approximately 24-48 hours. PEA-III-H does release the entire protein load in the first week. PEA-III-Bz in fact does release only a small fraction of the loaded protein during the first days and then the release stops. These properties correlate with swelling data as well. While the polyesteramide with two different pendant functional groups, swells very little in the first weeks and constantly releases proteins over 20 weeks.

In the following embodiments of the present invention n in Formula (I) preferably varies from 50-200 and m, p and q units in the backbone of the polyesteramide of formula (I) are in a random distribution.

In a preferred embodiment the biodegradable polyesteramide copolymer according to Formula (I) comprises p=0 and m+q=1, m=0.75, b is 0.5 and a+b=1 whereby $R_1$ is $(CH_2)_8$, $R_3$ is $(CH_3)_2$—CH—$CH_2$—, $R_5$ is hexyl, $R_7$ is alpha-amino acid used in synthesis is L-phenylalanine. In alternatives wherein the $R_3$s or $R_4$s are —$CH_2$—$CH(CH_3)_2$, the co-polymer contains the natural amino acid leucine. By independently varying the $R_3$s and $R_4$s within variations of the two co-monomers as described herein, other natural alpha-amino acids can also be used, e.g., glycine (when the $R_3$s or $R_4$s are H), alanine (when the $R_3$s or $R_4$s are $CH_3$), valine (when the $R_3$s or $R_4$s are $CH(CH_3)_2$), isoleucine (when the $R_3$s or $R_4$s are $CH(CH_3)$—$CH_2$—$CH_3$), phenylalanine (when the $R_3$s or $R_4$s are $CH_2$—$C_6H_5$), lysine (when the $R_3$s or $R_4$s $(CH_2)_4$—$NH_2$); or methionine (when the $R_3$s or $R_4$s are —$(CH_2)_2S(CH_3)$, and mixtures thereof.

Examples of proteins are cytokines & antagonists, peptides, hormones, antibodies, enzymes, fusion proteins or coagulation factors & inhibitors. Specific examples of cytokines & antagonists are Interferon alfacon-1, Interferon alfacon-2a, Interferon alfacon-2b, Interferon beta-1a, Interferon beta-1b, Aldesleukin (IL-2), Filgastim (G-CSF), Lenograstim (G-CSF), Molgramostim (G-CSF), Sargramostim (G-CSF), Tasonermin (TNF-α), Becaplermin (PDGF-BB), Oprevelkin (IL-11) or Anakinra (IL-1-RA). Specific examples of peptides and hormones are Insulin, Epoetin alfa, Epoetin beta, Folitropin alfa, Folitropin beta, Somatropin, Glucagon, Teriparatide (PTH 1-34), Salmon Calcitonin, Thyrotropin-alfa, Chorigondotropin A2, Osteogenic protein-1, Dibotermin alfa, Pegvisomant (hGH antagonist), Nesiritide (natriuretic peptide) or Lutropin alfa. Specific examples of antibodies are Abciximab, Adalimumab, Alemtuzumab, Arcitumomab, Basiliximab, Bevacizumab, Gemtuzumab, Ibritumomab, Infliximab, Palivizumab, Rituximab, Trastuzumab, Omalizumab, Efalizumab, Catuximab, Daclizumab, Pantimumab or Ranibizumab. Specific examples of enzymes are Alteplase (t-PA), Reteplase, Tenecteplase (TNK-t-P), Monteplase, Dornase-alfa (RNase), Imiglucerase, Agalsidase alfa & beta, Laronidase or Rasburicase. Specific examples of coagulation factors & inhibitors are Eptacog alfa, Antihemophilic Factor (3), Moroctocog alfa, (FVIII mutein), Desirudin, Lepirudin, Drotrecogin-alfa (Protein C act.) or α1 Proteinase inhibitor. Specific examples of fusion proteins are Denileukin diftitox, Etanercept or Alefacept Other examples of proteins are oxytocin, vasopressin, adrenocorticotropic hormone, epidermal growth factor, platelet-derived growth factor (PDGF), prolactin, luteinizing hormone releasing hormone (LHRH), LHRH agonists, LHRH agonists, growth hormones (including human, porcine, and bovine), growth hormone releasing factor, insulin, erythropoietin (including all proteins with erythropoietic activity), somatostatin, glucagon, interleukin (which includes IL-2, IL-11, IL-12, etc.), gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hank, glucagon-like peptide (GLP-1), renin, bradykinin, bacitracins, polymyxins, colistins, tyrocidine, gramicidins or cyclosporins.

The drug delivery composition according to the present invention may for example comprise from 0.1 wt % to 99.9 wt % of protein and from 99.9 wt % to 0.1 wt % of biodegradable polymer based on the total weight of the composition. Preferably the composition comprises from 0.1 wt % to 20 wt % of protein and from 60 wt % to 99.9. wt % of biodegradable polymer based on the total weight of the composition.

As used herein, the term "alkyl" refers to a straight or branched chain hydrocarbon group including methyl, ethyl, n-propyl, isopropyl, n-butyl, isobutyl, tert-butyl, n-hexyl, and the like.

As used herein, the term "alkylene" refers to a divalent branched or unbranched hydrocarbon chain containing at least one unsaturated bond in the main chain or in a side chain including methylene, ethylene, propylene, butylene and the like.

As used herein, "alkynyl", refers to straight or branched chain hydrocarbon groups having at least one carbon-carbon triple bond.

As used herein the term biodegradable" refers to material which is capable of being completely or substantially degraded or eroded when exposed to an in vivo environment or in vitro. A polymer is capable of being degraded or eroded when it can be gradually broken-down, resorbed, absorbed and/or eliminated by, for example, hydrolysis, enzymolysis, oxidation, metabolic processes, bulk or surface erosion within a subject. The terms "bioabsorbable" and "biodegradable" are used interchangeably in this application.

As used herein the term "random" as used herein refers to the distribution of the m, p and q units of the polyesteramide of formula (I) in a random distribution.

As used herein "protein" is intended to include one of a group of complex organic compounds which contain carbon, hydrogen, oxygen, nitrogen, and sometimes sulfur.

As used herein "biological environment" shall mean any environment, whether in vitro or in vivo, where biological activity may be controlled.

The polyesteramide co-polymers preferably have an average number molecular weight (Mn) ranging from 15,000 to 200,000 Daltons. The polyesteramide co-polymers described herein can be fabricated in a variety of molecular weights and a variety of relative proportions of the m, p, and q units in the backbone. The appropriate molecular weight for a particular use is readily determined by one skilled in the art. A suitable Mn will be in the order of about 15,000 to about 100,000 Daltons, for example from about 30,000 to about 80,000 or from about 35,000 to about 75,000. Mn is measured via GPC in THF with polystyrene as standard.

The basic polymerization process of polyesteramides is based on the process described by G. Tsitlanadze, et al. J. Biomater. Sci. Polym. Edn. (2004) 15:1-24, however different building blocks and activating groups were used.

The polyesteramides used in the composition of the present invention are for example synthesized as shown in scheme 1; via solution polycondensation of para-toluene sulfonate di-amines salts (X1, X2, X3, X4) with activated di-acids (Y1). Typically dimethylsulfoxide or dimethylformamide are used as solvent. Generally as a base 1.1 eq triethylamide is added with respect to the amount of para-toluene sulfonate, the reaction is carried out under an inert atmosphere at 60° C. for 24-72 hours under constant stirring. Subsequently the obtained reaction mixture is purified via a water precipitation followed by an organic precipitation and filtration. Drying under reduced pressure yields the polyesteramide.

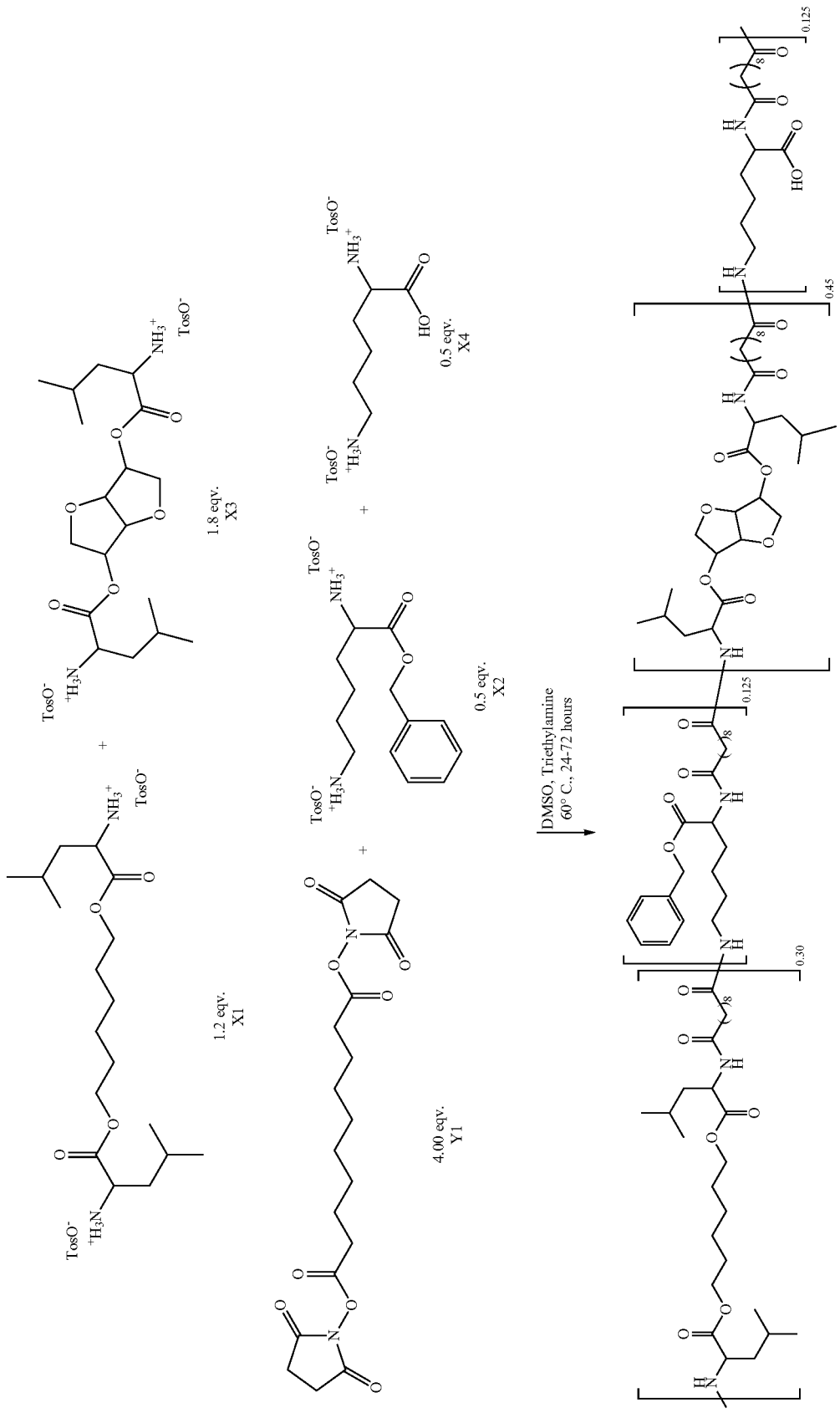

Typically, the drug delivery compositions of the present invention may comprise more than one protein. Alternatively, multiple types of proteins can be present as part of a single formulation. For example, a second protein can be present.

The drug delivery composition of the present invention may also comprise a further bioactive agent other than a protein. Such bioactive agent may include small molecule drugs, sugars, lipids or whole cells. The bioactive agents can have antiproliferative or anti-inflammatory properties or can have other properties such as antineoplastic, antimitotic, antibiotic, antiallergic, or antioxidant properties. Examples of antiproliferative agents include rapamycin and its functional or structural derivatives, 40-O-(2-hydroxyl)ethyl-rapamycin (everolimus), and its functional or structural derivatives, paclitaxel and its functional and structural derivatives. Examples of antineoplastics and/or antimitotics include methotrexate, azathioprine, vincristine, vinblastine, fluorouracil, doxorubicin hydrochloride (e.g. Adriamycin® from Pharmacia AND Upjohn, Peapack N.J.), and mitomycin (e.g. Mutamycin® from Bristol-Myers Squibb Co., Stamford, Conn.). Examples of such antiplatelets include sodium heparin, low molecular weight heparins, heparinoids, hirudin, argatroban, forskolin, vapiprost, dextran, D-phe-pro-arg-chloromethylketone (synthetic antithrombin), dipyridamole, glycoprotein Hb/nia platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck AND Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents include steroidal and nonsteroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck AND Co., Inc., Whitehouse Station, N.J.). An example of an antiallergic agent is permirolast potassium.

The drug delivery composition may also include further polymers beside the biodegradable polyesteramide of Formula I. It may for example be blended with poly(ortho esters), poly(anhydrides), poly(D,L-lactic acid), poly(L-lactic acid), poly(glycolic acid), copolymers of poly(lactic) and glycolic acid, poly(L-lactide), poly(D,L-lactide), poly(glycolide), poly(D,L-lactide-co-glycolide), poly(L-lactide-co-glycolide), poly(phospho esters), poly(trimethylene carbonate), poly(oxa-esters), poly(oxa-amides), poly(ethylene carbonate), poly(propylene carbonate), poly(phosphoesters), poly(phosphazenes), poly(tyrosine derived carbonates), poly(tyrosine derived arylates), poly(tyrosine derived iminocarbonates), copolymers of these polymers with poly (ethylene glycol) (PEG), or combinations thereof. It is of course also possible that more than one polyesteramides of formula (I) is mixed together or that the polyesteramides of Formula I are blended with other polyesteramides.

The drug delivery composition may also comprise further excipients such as for example fillers, anti-oxidants, stabilizers, anti-caking agents, emulsifiers, foaming agents, sequestrants or dyes.

The composition of this invention can be administered to any biological environment, whether in vitro or in vivo, where controlled protein delivery is desired. For example, the composition could be administered to a human, or to animal, by injection and/or implantation subcutaneously, intramuscularly, intra-peritoneally, intra-dermally, intravenously or intra-arterially by administration to mucosal membranes, or by in situ delivery to provide the desired dosage of protein based on the known parameters for treatment of the various medical conditions.

The drug delivery composition of the present invention can be used in the medical field of management of pain, musculoskeletal applications (MSK), ophthalmology, oncology, dermatology, cardiovascular field, orthopedic, spinal, intestinal, pulmonary, nasal or auricular field.

The present invention further relates to articles comprising the drug delivery composition of the present invention. In another aspect, the invention provides for a drug delivery system comprising the drug delivery composition of the present invention. In the context of the present invention a drug delivery system includes but is not limited to microparticles, nanoparticles, rods, films, fibers, pellets, cylinders, discs, coatings, implants, microcapsules, wafers, micelles, liposomes, woven and non-woven fabrics.

FIGURES

FIG. 1: Mass gain over time of PEA films after immersion in PBS buffer.

Figure 2:
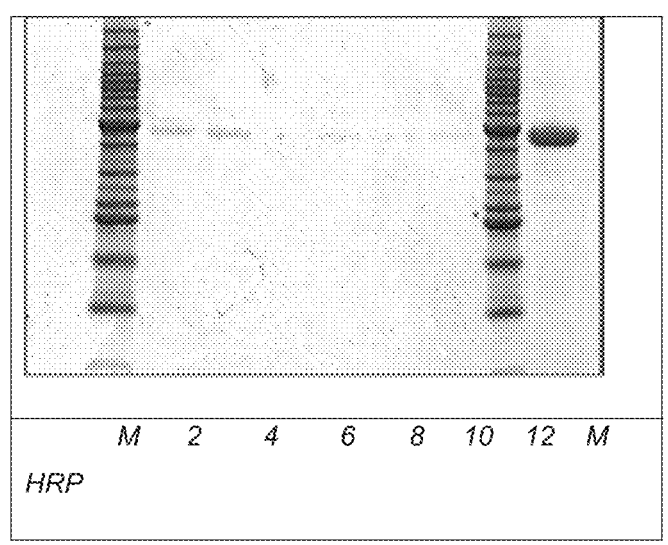

FIG. 2: Release of HRP determined with SDS-PAGE. M=protein marker, HRP=horseradish peroxide standard, 2-12=HRP release buffer taken after 2-12 weeks.

Figure 3:
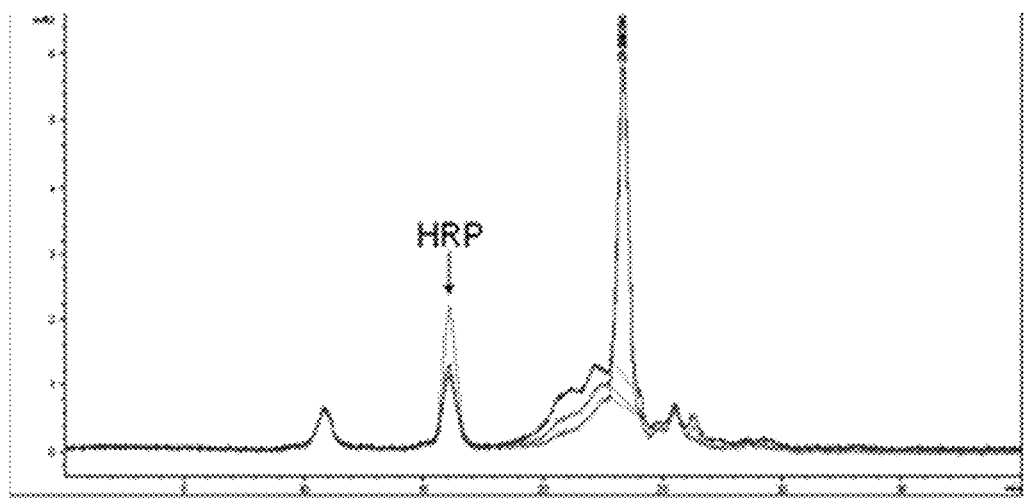

FIG. 3: SEC chromatogram overlay of several release media of PEA III X50. The peak at 10 minutes originates from the buffer, HRP elutes at 16 minutes, small molecules elute at 20-25 minutes.

Figure 4:
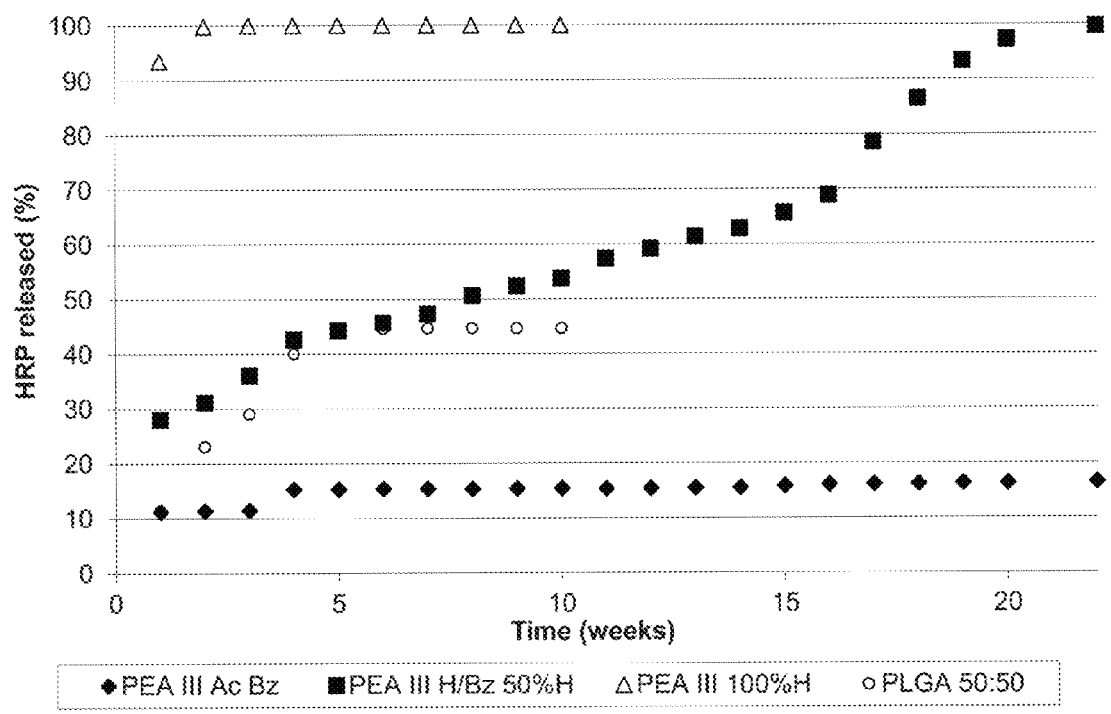

FIG. 4: Cumulative release of HRP from polymeric matrices over 22 weeks.

Figure 5:
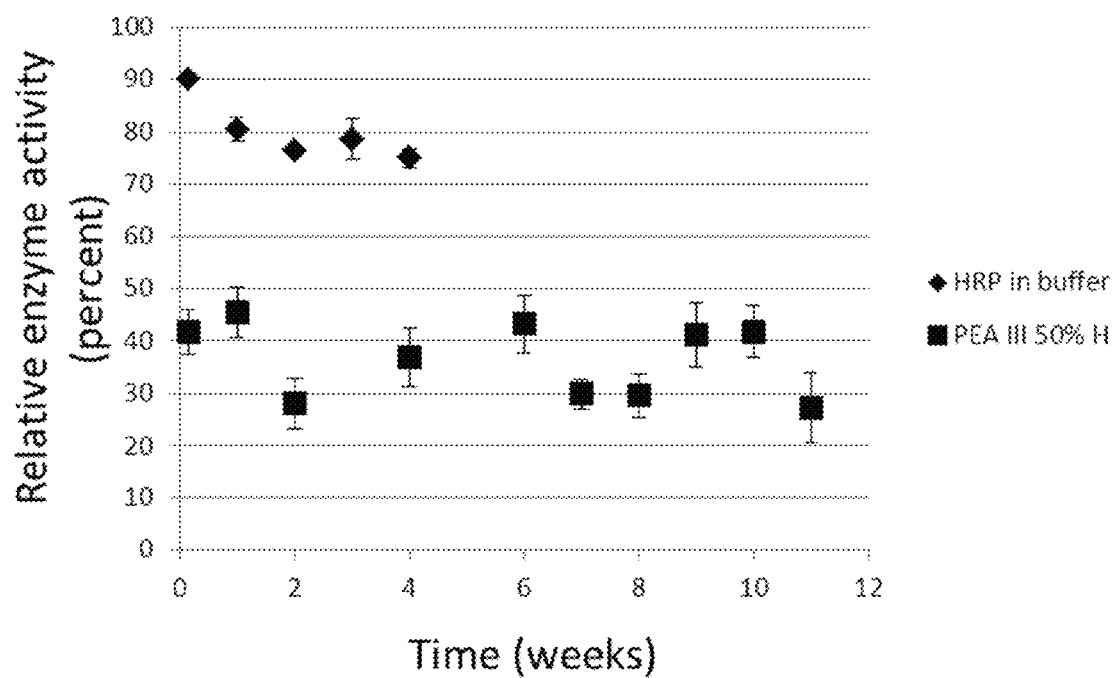

FIG. 5: Enzyme stability in the polymer matrix.

Figure 6:
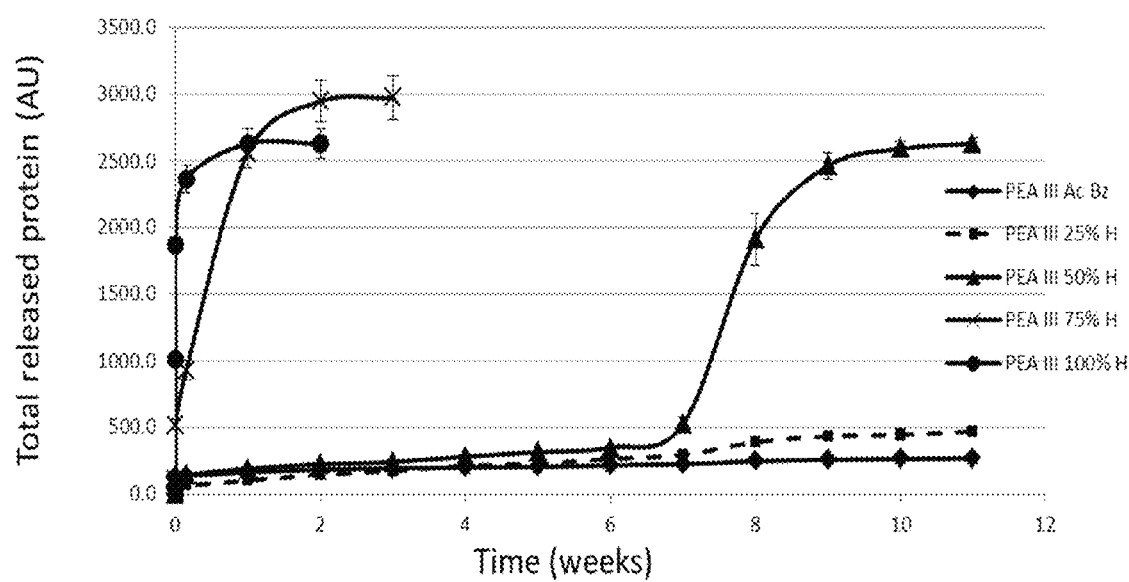

FIG. 6: Protein release from PEA matrices. The figure shows that PEA polymers of analogous monomer composition which possess either only free carboxyl groups or only benzyl esters do not provide sustain protein release. In contrast, by varying the relative ration of the side groups in the polymer chain we can get control over the release profile of the protein species.
PEA III 100% H (polymer with only —COOH side groups)—the polymer fibers release the entire polymer load in the first several hours—typical burst release)
PEA III Ac Bz (polymer with only benzyl ester side groups)—The polymer does not release significant amount of protein and the release properties of the fiber does not change over time.
PEA III 75% H—Polymer fibers do release the entire protein load over three weeks and the activity of the released enzyme does not change along the release.
PEA III 50% H—Polymer fibers do release the protein load between week 3 and week 11 with majority of the enzyme released between week 6 and week 10. The activity of the released enzyme does not change along the release.

PEA III 25% H—Polymer fibers do start substantially to release in week 7. The release is not completed in the 11 weeks period of the experiment.

The present invention will now be described in detail with reference to the following non limiting examples which are by way of illustration only.

EXAMPLES

Example 1

Swelling Behavior of PEA-III-H/Bz Copolymers

The swelling behavior of PEA-III-Ac Bz (possessing pendant ester groups along the polymer chain), PEA-III-H/Bz 25% H (possessing both pendant ester and carboxyl groups), PEA-III-H/Bz 50% H (possessing both pendant ester and carboxyl groups) and PEA-III-H possessing pendant carboxyl groups were assessed on round polymeric films, prepared via solvent casting. The films were immersed in PBS buffer which contained 0.05% NaN$_3$ as a biocide and were placed at 37° C. under gentle agitation. The swelling behavior was assessed based on the mass gain of the polymer films. The buffers were refreshed on each time point.

Mass gain can be calculated according to the following Formula;

$$\text{mass gain}(\%) = \frac{M_t - M_0}{M_0} * 100\%$$

$M_t$=mass at time point (t)
$M_0$=initial mass

Films of PEA-III-Ac-Bz showed marginal swelling, up to 5% over the test period. In contrast PEA-III-H films gained mass up to 1000% compared to the original mass within a few days. Surprisingly films made from PEA-III-H/Bz 25% H and PEA-III-H/Bz 50% H showed a slow and sustained water absorption profile. This is shown in FIG. 1.

Example 2

ABTS Activity Assay for HRP

ABTS (2,2'-azino-bis(3-ethylbenzothiazoline-6-sulphonic acid) is generally used as an activity assay for peroxidase activity (e.g. for HRP=horseradish peroxide). The assay is based on the formation of highly colored oxidized/radical form of the substrate that can be quantified photometric. The formation of the highly colored product is a direct measure for the activity of the measured enzyme. In scheme 1 the reaction of ABTS is shown.

Scheme 1: the reaction scheme of ABTS with a peroxidase (e.g. HRP). The product is highly colored and has an absorption maximum at 405 nm and can be qualified photometrical.

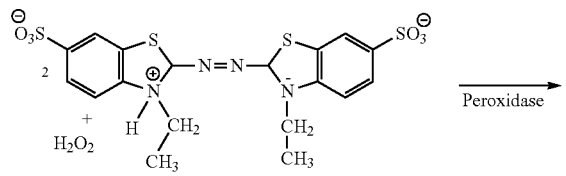

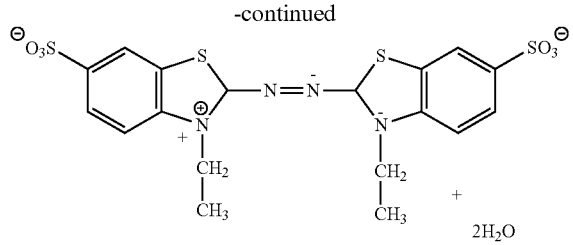

The protocol for the assay was adapted from Putter, J. and Becker, R. (1983) *Methods of Enzymatic Analysis* (Bergmeyer, H. U., ed.) 3rd ed., Vol III, pp. 286-293, Verlug Chemie, Deerfield Beach, Fla.

A stock solution of ABTS with a concentration of 5 mg/mL was prepared in PBS buffer. A stock solution of 0.3 wt % H$_2$O$_2$ in water was prepared. In the reference cuvet 1 mL of the ABTS stock and 50 μL of the H$_2$O$_2$ stock were mixed. In the sample cuvet 1 mL of the ABTS stock and 50 μL of the H$_2$O$_2$ stock were mixed with 50 μL of the enzyme solution. The cuvet was directly placed in the photometer and the absorbance increase at 405 nm was measured over one minute with a time interval of 0.5s. The steepness of the absorbance increase is a measure for the activity of the enzyme and was determined based on the digital data of the photometer using Microsoft Excel. Eventually the activity of the enzyme was correlated to a concentration based on the activity of freshly prepared HRP solution and used for quantification.

Example 3

SDS-PAGE

All sodiumdodecyl sulfate (SDS) reagents and gels were obtained from Life Technologies (NuPAGE system). Release samples were mixed with 4×SDS loading buffer and 10× reducing agent. Protein denaturation was achieved by 5 minutes heating to 70° C. Typically 20 μl sample was loaded on the gel. 12% Bis-Tris or 4-12% Bis-Tris gels were used with MOPS or MES buffer, respectively. For detect of HRP (>1 ug), Coomassie staining (SimplyBlue safestain) was applied. Release media of PEA-III-50% H were analyzed using SDS-PAGE. In the illustration several release samples of HRP are shown. It can be observed that the released enzyme appears on the same spot as the HRP standard, confirming the release of the enzyme. This is shown in FIG. 2

Example 4

Aqueous SEC

HRP release buffers were analyzed using an Agilent 1200 LC system equipped with a TSK gel G2000SWXL 7.8*300 mm (TOSOH Bioscience) column using DAD detection. The system was operated with a flow rate of 0.5 mL/min using 1.059 mM KH$_2$PO$_4$, 2.966 mM Na$_2$HPO$_4$, 300 mM NaCl, pH=7.4 and 10% EtOH as the mobile phase. A typical sample injection volume of 10 μL was used.

DAD data obtained from several different release buffers of PEA III 50% H are illustrated and were used for quantification of the enzyme as complementary method to the ABTS activity assay. Both methods showed good correlation (90-110%) indicating that the released enzyme retained full activity. The peak at 10 min is also present in the blank and is not associated with the sample.

FIG. 3 Illustration: SEC chromatogram overlay of several release media of PEA III X50. The peak at 10 minutes originates from the buffer, HRP elutes at 16 minutes, small molecules elute at 20-25 minutes.

Example 5

Release of Horseradish Peroxidase (HRP) from Polymeric Matrices Processing and Loading 400 µL of a 10 wt % polymer solution in $CHCl_3$ of PLGA 50:50, PEA-III-Ac Bz (possessing pendant ester groups along the polymer chain), PEA-III-H/Bz 50% H (possessing both pendant ester- and carboxyl groups) and PEA-III-100% H (possessing pendant carboxyl groups) was added to 2 mg lyophilized HRP. The HRP was mechanically dispersed in the solutions. The obtained suspensions of polymer and HRP were dried under reduced pressure at ambient temperature.
Release of HRP Dry HRP loaded films were immersed in 3 mL PBS buffer and placed at 37° C. under gentle agitation. Over time the released HRP was quantified both with aqueous SEC and with a photometric activity assay using ABTS as the reagent. After one week the concentration of HRP was determined in the buffers with both methods. The data from both methods correlated well, indicating that the released HRP was active. PEA-III-100% H released already the majority of all HRP present in the film in the first week after 3 weeks the film was completely empty. From the PEA-III-Ac Bz practically no release was observed over the test period apart from the release in the first week. PLGA 50:50 showed release of HRP over a period of 5 weeks after that no active protein was released anymore. After 8 weeks the PLGA 50:50 matrix was completely degraded without any further release. Surprisingly from the PEA-III-H/Bz 50% H film active HRP was released over a time frame of 22 weeks with a relatively constant rate.

It was observed that the release of HRP from the PEA films was in line with the water absorption properties of the subsequent polymers. The experiment shows the role of both types of pendant functional groups along the polymer chain. Only the composition comprising the polyesteramide comprising simultaneously both pendant ester and carboxyl groups (PEA-III-H/Bz 50% H) allows a complete and sustained release of the protein over a long period. Analysis of the polymer matrix after 22 weeks showed that no significant amount of enzyme is present confirming the hypothesis for complete release of the protein.

PEA-III-100% H swells fast and released the HRP very fast, PEA-III-Ac-Bz shows a marginal swelling and almost no release of HRP, PEA-III-H/Bz 50% illustrates a gradual swelling in combination with a sustained release of HRP with an increased release rate beyond week 17. This is shown in FIG. 4.

Example 6

Preparation of HRP Loaded PEA Polymer Fibres

PEA-III-25% H polymer was dissolved in ethanol, methanol, chloroform, or dichloromethane for the experiments that tested the influence of solvents. For the release study PEA-III-AcBz and PEA-H/Bz polymers were dissolved in ethanol. Polymers solutions were prepared at a concentration of 10% (w/v). Subsequently, HRP was added under vigorous stirring in a Teflon beaker. After obtaining a homogeneous solution the solvent was allowed to evaporate. When the polymers became solid enough to manipulate they were transferred onto a Teflon sheet. The polymers were then shaped manually into a fibre by rolling it in between Teflon sheets and blocks. The fibers had a diameter between 0.8 and 1.2 mm and were 3 cm in length.

Fibres were allowed to dry in ambient conditions for 5 days before being used. Fibres for the release of HRP #P6782 were then cut to be used as triplicates in the release experiments. HRP used was Sigma #P6782.
Release of HRP Release experiments were carried out in Dulbecco's Phosphate Buffered Saline (PBS) under continuous shaking at ±100 rpm at 37° C. HRP loaded PEA-III-AcBz, 25% H, 50% H, 75% H or 100% H were weight and analysed under the microscope before start of the experiments. All fibres had mass of about 50 mg (±5 mg). The first day buffer exchanged after 2, 5 and 24 hours and after that once a week. The old buffer was then analysed for protein quantity and HRP activity.

FIG. 5 shows that the activity of the enzyme released from the polymer matrix remains at the same level over the entire 11 weeks period of the experiment. This suggests that neither polymer matrix nor the polymer degradation products do impact on enzyme activity and stability.

FIG. 6 shows that PEA polymers of analogous monomer composition which possess either only free carboxyl groups or only benzyl esters do not provide sustain protein release. In contrast, by varying the relative ration of the side groups in the polymer chain we can get control over the release profile of the protein species.
PEA-III-100% H (polymer with only —COOH side groups)—the polymer fibers release the entire polymer load in the first several hours—typical burst release)
PEA-III-Ac Bz (polymer with only benzyl ester side groups)—The polymer does not release significant amount of protein and the release properties of the fiber does not change over time.
PEA-III-75% H—Polymer fibers do release the entire protein load over three weeks and the activity of the released enzyme does not change along the release.
PEA-III-50% H—Polymer fibers do release the protein load between week 3 and week 11 with majority of the enzyme released between week 6 and week 10. The activity of the released enzyme does not change along the release.
PEA-III-25% H—Polymer fibers do start substantially to release in week 7. The release is not completed in the 11 weeks period of the experiment
Protein Analysis
Quantification:

Release samples were analysed using the BCA Quantipro assay (Sigma Aldrich) according to manufacturer's instructions. As a control, release samples from empty fibres (without HRP) were also analysed because PEA can give small signal when degrading. When necessary this signal was subtracted from the actual release samples. The BCA assay was measured with a Multiscan GO plate reader (Thermo Scientific).
Activity Assay:

A stock solution of ABTS (2,2'-azino-bis(3-ethylbenzothiazoline-6-sulphonic acid) (Sigma # A1888) with a concentration of 5 mg/mL was prepared in PBS buffer. A stock solution of 0.3 wt % $H_2O_2$ in water was prepared. In the reference cuvette 1 mL of the ABTS stock and 50 µL of the $H_2O_2$ stock were mixed. In the sample cuvette 1 mL of the ABTS stock and 50 µL of the $H_2O_2$ stock were mixed with 50 µL of the sample solution. The cuvette was directly placed in the photometer (Shimadzu UV-1800) and the absorbance increase at 405 nm was measured over one minute. The slope of absorbance was used to measure the activity of the enzyme. Assay was carried out at room temperature.

Swelling Behaviour:

Films (thickness 0.5 mm) of each polymer were prepared and dried under reduced pressure to reduce the water content of the tested materials below 0.3% (w/w). Discs with a diameter of 4 mm and a thickness of 0.5 mm were punched from the films.

Prior to the incubation in PBS buffer (2 mL), samples were weighted on Sartorius micro balance and both thickness and diameter were recorded. Samples were immersed in 5 mL 10 mM PBS buffer, pH 7.4 containing 0.05% (w/w) $NaN_3$. All polymer samples were incubated at 37° C. the water uptake was evaluated by measuring the sample weight increase at different time points. The weight increase was measured as follows:

Samples were taken out of the buffer solution and dried on dust-free absorbing paper (without pressing) in order to remove the adhering water from the discs. Next the samples were analysed by Sartorius micro balance and readouts were recorded. Each polymer sample has been analysed in triple. The weight was then compared to the original weight. The original weight was set as a 100%. At the read out time points buffer solutions were refreshed.

The figure shows that the activity of the enzyme released from the polymer matrix remains at the same level over the entire 11 weeks period of the experiment. This suggests that neither polymer matrix nor the polymer degradation products do impact on enzyme activity and stability.

The invention claimed is:

1. A drug delivery composition which comprises, based on total weight of the composition:
   at least 0.1 wt. % to 99 wt. % of a protein, and from 99.9 wt. % to 0.1 wt. % of a biodegradable polymer, wherein the biodegradable polymer comprises at least two different functional groups being unprotected hydrophilic groups and protected hydrophobic groups pendant to the polymer backbone, which functional groups are selected from the group of carboxyl, amine, hydroxyl, ester, amide, thiol or thioester groups, and wherein the unprotected hydrophilic groups and the protected hydrophobic groups are present in a ratio of the unprotected hydrophilic groups to the protected hydrophobic groups of 0.17-3, and wherein
   the polymer absorbs between 2-20% w/w water if exposed to physiological conditions for at least 20 days.

2. The drug delivery composition according to claim 1, wherein the two different functional groups comprise at least an unprotected hydrophilic functional group selected from a carboxyl group, an amine group, a thiol group or a hydroxyl group, and at least a protected hydrophobic functional group selected from an ester group, an amide group or a thioester group.

3. The drug delivery composition according to claim 2, wherein the biodegradable polymer possesses pendant carboxyl and ester functional groups.

4. The drug delivery composition according to claim 1, wherein the biodegradable polymer is a polyesteramide.

5. The drug delivery composition according to claim 4, wherein the polyesteramide is a polyesteramide copolymer according to structural Formula (I):

Formula I

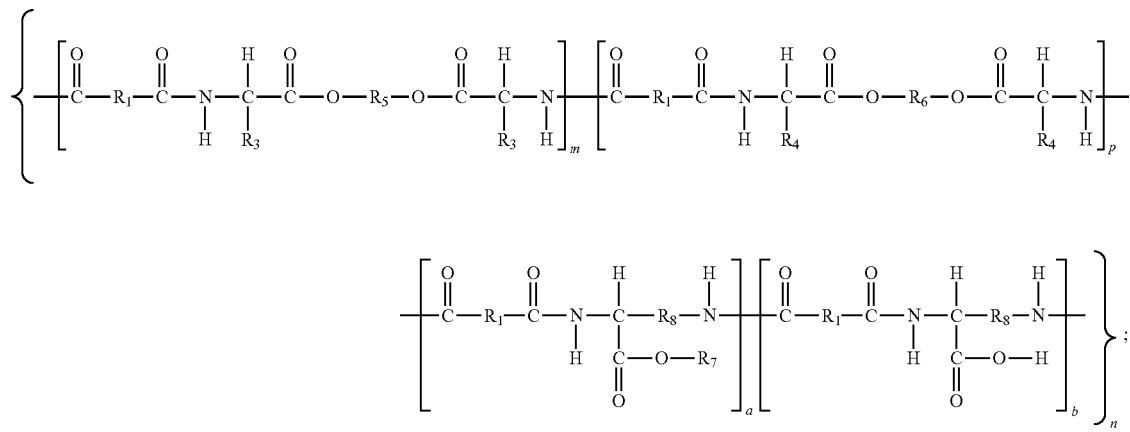

wherein m+p varies from 0.9-0.1 and a+b varies from 0.1 to 0.9; m+p+a+b=1, wherein m or p could be 0; n varies from 5 to 300 and wherein a is at least 0.01, b is at least 0.015 and the ratio of a to b (a:b) is from 0.1:9 to 0.85:0.15, wherein the m unit and/or p unit, and the a and b units, are randomly distributed; and wherein:

$R_1$ is independently selected from the group consisting of $(C_2\text{-}C_{20})$ alkyl, $R_3$ and $R_4$ in a single backbone unit m or p, respectively, are independently selected from the group consisting of hydrogen, $(C_1\text{-}C_6)$alkyl, $(C_2\text{-}C_6)$alkenyl, $(C_2\text{-}C_6)$alkynyl, $(C_6\text{-}C_{10})$aryl, $(C_1\text{-}C_6)$alkyl, $—(CH_2)SH$, $—(CH_2)_2S(CH_3)$, $(CH_3)_2—CH—CH_2—$, $—CH(CH_3)_2$, $—CH(CH_3)—CH_2—CH_3$), $—CH_2—C_6H_5$, $—(CH_2)_4—NH_2$, and mixtures thereof;

$R_5$ is independently selected from the group consisting of $(C_2\text{-}C_{20})$alkyl, $(C_2\text{-}C_{20})$alkylene, $R_6$ is selected from bicyclic-fragments of 1,4:3,6-dianhydrohexitols of structural formula (II);

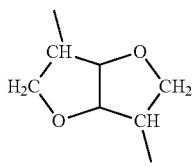

Formula II $R_7$ is independently selected from the group consisting of $(C_6-C_{10})$ aryl $(C_1-C_6)$ alkyl or a protecting group; and —$R_8$ is —$(CH_2)_4$—.

6. The drug delivery composition according to claim 5, wherein b is at least 0.025 and a:b is from 0.1:0.9 to 0.75:0.25.

7. The drug delivery composition according to claim 5, wherein b is at least 0.05 and a:b is from 0.1:0.9 to 0.5:0.5.

8. The drug delivery composition according to claim 5, wherein p=0 and m+a+b=1, m=0.75, b is 0.125 and a+b=0.25, wherein $R_1$ is $(CH_2)_8$, $R_3$ is $(CH_3)_2$—CH—$CH_2$—, $R_5$ is hexyl, $R_7$ is benzyl, $R_8$ is —$(CH_2)_4$—.

9. The drug delivery composition according to claim 5, wherein m+p+a+b=1, a+b=0.25, p=0.45 and m=0.3, b is 0.0625, wherein $R_1$, —$(CH_2)_8$; $R_3$ and $R_4$ respectively, are $(CH_3)_2$—CH—$CH_2$—, $R_5$ is selected from the group consisting of $(C_2-C_{20})$alkylene, $R_7$ is benzyl, $R_8$ is —$(CH_2)_4$—; $R_6$ is selected from bicyclic-fragments of 1,4:3,6-dianhydrohexitols of structural formula (II).

10. The drug delivery composition according to claim 5, wherein m+p+a+b=1, a+b=0.25, p=0.45 and m=0.3, b is 0.125, wherein $R_1$ is —$(CH_2)_8$; $R_4$ is $(CH_3)_2$—CH—$CH_2$—, $R_7$ is benzyl, $R_8$ is —$(CH_2)_4$—; $R_6$ is selected from bicyclic-fragments of 1,4:3,6-dianhydrohexitols of structural formula (II).

11. The drug delivery composition according to claim 5, wherein m+p+a+b=1, a+b=0.1, p=0.30 and m=0.6, b is 0.05, wherein $R_1$—$(CH_2)_4$; $R_3$ and $R_4$ respectively, are $(CH_3)_2$—CH—$CH_2$—; $R_7$ benzyl, $R_8$ is —$(CH_2)_4$—; $R_5$ is selected from the group consisting of $(C_2-C_{20})$alkylene, $R_6$ is selected from bicyclic-fragments of 1,4:3,6-dianhydrohexitols of structural formula (II).

12. The drug delivery composition according to claim 1, wherein the protein is at least one selected from the group consisting of peptides, insulin, hormones, vaccines, enzymes, antibiotics, antibodies, neuroactive agents, growth factors, cytokines, antigens and glycoproteins.

13. A drug delivery system for controlled protein release comprising the composition according to claim 1.

14. The drug delivery system according to claim 13, wherein the drug delivery system is in a form comprising microparticles, films, coatings, fibers, pellets, cylinders, discs, implants, microcapsules, microspheres, nanospheres, wafers, micelles, liposomes, woven or non-woven fabrics.

15. The drug delivery composition according to claim 2, wherein the unprotected hydrophilic groups and the protected hydrophobic groups are present in a ratio of the unprotected hydrophilic groups to the protected hydrophobic groups of 0.3-1.

16. The drug delivery composition according to claim 3, wherein the unprotected hydrophilic groups and the protected hydrophobic groups are present in a ratio of the unprotected hydrophilic groups to the protected hydrophobic groups of 0.3-1.

17. The drug delivery composition according to claim 2, wherein the composition comprises from 0.1 wt% to 20 wt% of the protein and from 60 wt% to 99.9 wt% of the biodegradable polymer.

18. The drug delivery composition according to claim 3, wherein the composition comprises from 0.1 wt% to 20 wt% of the protein and from 6 wt% to 99.9 wt% of the biodegradable polymer.

19. The drug delivery composition according to claim 5, wherein the composition comprises from 0.1 wt% to 20 wt% of the protein and from 60 wt% to 99.9 wt% of the biodegradable polymer.

20. The drug delivery composition according to claim 8, wherein the composition comprises from 0.1 wt% to 20 wt% of the protein and from 60 wt% to 99.9 wt% of the biodegradable polymer.

* * * * *